US010517659B2

(12) United States Patent
Sixto et al.

(10) Patent No.: US 10,517,659 B2
(45) Date of Patent: Dec. 31, 2019

(54) BONE FIXATION SYSTEMS, DEVICES, AND METHODS

(71) Applicant: Biomet Manufacturing, LLC, Warsaw, IN (US)

(72) Inventors: Robert Sixto, Miami, FL (US); Juergen A Kortenbach, Miami Springs, FL (US); Elizabeth Perepezko, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 16/255,244

(22) Filed: Jan. 23, 2019

(65) Prior Publication Data
US 2019/0150997 A1 May 23, 2019

Related U.S. Application Data

(62) Division of application No. 15/136,812, filed on Apr. 22, 2016, now Pat. No. 10,219,847.
(Continued)

(51) Int. Cl.
*A61B 17/80* (2006.01)
*A61L 27/06* (2006.01)
(Continued)

(52) U.S. Cl.
CPC ...... *A61B 17/8057* (2013.01); *A61B 17/8605* (2013.01); *A61B 17/866* (2013.01);
(Continued)

(58) Field of Classification Search
CPC ............ A61B 17/8057; A61B 17/866; A61B 17/8605; A61B 17/8625; A61L 27/06; A61L 31/022; C22C 14/00
See application file for complete search history.

(56) References Cited

U.S. PATENT DOCUMENTS 6,783,529 B2  8/2004 Hover et al.
8,066,706 B2  11/2011 Schlienger et al.
(Continued)

FOREIGN PATENT DOCUMENTS

WO   WO-2016172601 A1   10/2016

OTHER PUBLICATIONS

"U.S. Appl. No. 15/136,812, Examiner Interview Summary dated Oct. 9, 2018", 3 pgs.
(Continued)

*Primary Examiner* — Jessee R Roe
(74) *Attorney, Agent, or Firm* — Schwegman Lundberg & Woessner, P.A.

(57) ABSTRACT

Various systems, devices, and methods for improved bone fixation are disclosed. The system includes a bone plate and a plurality of variable angle screws. The bone plate comprises titanium and the variable angle screws comprise a TiMo alloy treated to have a hardness of at least 35 HRC. A method of manufacturing an implant is also disclosed. The method includes machining the TiMo alloy having a first hardness value and a first % elongation to form an implant; heat treating, quenching, and ageing the bone fastener to have a second hardness value that can be greater than the first hardness value and a second % elongation that can be both less than the first % elongation and greater than about 3% elongation.

20 Claims, 5 Drawing Sheets

Related U.S. Application Data

(60) Provisional application No. 62/152,311, filed on Apr. 24, 2015.

(51) Int. Cl.
| | | |
|---|---|---|
| *A61B 17/86* | (2006.01) | |
| *C22C 14/00* | (2006.01) | |
| *A61L 31/02* | (2006.01) | |
| *C22F 1/00* | (2006.01) | |
| *C22F 1/18* | (2006.01) | |
| *A61B 17/00* | (2006.01) | |

(52) U.S. Cl.
CPC .......... *A61B 17/8625* (2013.01); *A61L 27/06* (2013.01); *A61L 31/022* (2013.01); *C22C 14/00* (2013.01); *C22F 1/002* (2013.01); *C22F 1/183* (2013.01); *A61B 2017/00526* (2013.01)

(56) References Cited

U.S. PATENT DOCUMENTS

| | | |
|---|---|---|
| 8,465,489 B2 | 6/2013 | Schlienger et al. |
| 2005/0234561 A1 | 10/2005 | Nutt et al. |
| 2005/0257864 A1 | 11/2005 | Marquardt et al. |
| 2007/0233100 A1 | 10/2007 | Metzinger |
| 2011/0180188 A1 | 7/2011 | Bryan |
| 2014/0018862 A1* | 1/2014 | Koay ................. A61B 17/8057 606/281 |
| 2016/0310182 A1 | 10/2016 | Sixto et al. |

OTHER PUBLICATIONS

"U.S. Appl. No. 15/136,812, Final Office Action dated Aug. 3, 2018", 8 pgs.

"U.S. Appl. No. 15/136,812, Non Final Office Action dated Apr. 16, 2018", 7 pgs.

"U.S. Appl. No. 15/136,812, Notice of Allowance dated Oct. 23, 2018", 8 pgs.

"U.S. Appl. No. 15/136,812, Response filed Feb. 28, 2018 to Restriction Requirement dated Jan. 5, 2018", 6 pgs.

"U.S. Appl. No. 15/136,812, Response filed Jul. 2, 2018 to Non Final Office Action dated Apr. 16, 2018", 10 pgs.

"U.S. Appl. No. 15/136,812, Response filed Oct. 15, 2018 to Final Office Action dated Aug. 3, 2018", 8 pgs.

"U.S. Appl. No. 15/136,812, Restriction Requirement dated Jan. 5, 2018", 6 pgs.

"U.S. Appl. No. PCT/US2016/029006, Invitation to Pay Additional Fees and Partial Search Report dated Jul. 15, 2016", 5 pgs.

"European Application Serial No. 16719734.2, Response filed Jun. 18, 2018 to Office Action dated Dec. 8, 2017", 10 pgs.

"International Application Serial No. PCT/US2016/029006, International Preliminary Report on Patentability dated Nov. 2, 2017", 10 pgs.

"International Application Serial No. PCT/US2016/029006, International Search Report dated Sep. 5, 2016", 6 pgs.

"International Application Serial No. PCT/US2016/029006, Written Opinion dated Sep. 5, 2016", 8 pgs.

Katthagen, J. C., et al., "Is there any advantage in placing an additional calcar screw in locked nailing of proximal humeral fractures?", Orthop Traumatol Surg Res 101, Abstract, (Jun. 2015), 2 pgs.

\* cited by examiner

BONE FIXATION SYSTEMS, DEVICES, AND METHODS

CLAIM OF PRIORITY

This application is a divisional of U.S. patent application Ser. No. 15/136,812, filed on Apr. 22, 2016, now U.S. Pat. No. 10,219,847, which claims the benefit of U.S. patent application Ser. No. 62/152,311, filed on Apr. 24, 2015, the benefit of priority of each of which is claimed hereby, and each of which is incorporated by reference herein in its entirety.

FIELD

The present disclosure relates to a variable angle titanium-molybdenum alloy bone fastener, and associated bone fixation systems and methods.

BACKGROUND

This section provides background information related to the present disclosure, which is not necessarily prior art.

Conventional bone fixation systems include titanium alloy plates and a variety of different types of bone fasteners, such as non-locking screws, fixed angle locking screws, and variable angle locking screws. Such bone fixation systems are difficult to provide in a single sterile package due to the number of different types of bone fasteners a surgeon can selectively use to tailor the application of the plate system to the specific nature of the fracture suffered by the individual patient. Furthermore, in the case of variable angle screws where the screw material must be harder than the plate material, material mismatch between the bone fasteners and the plates can give rise to a risk of fretting and galvanic corrosion. Accordingly, improved bone fixation systems, devices, and methods are desirable.

SUMMARY

This section provides a general summary of the disclosure, and is not a comprehensive disclosure of its full scope or all of its features.

The present inventors have recognized that reducing the number of types of screws corresponding to a bone fixation system can reduce the inventory of bone fasteners required for a fixation procedure and enable provision of such systems in a single, sterile package.

Additionally or alternatively, the present inventors have recognized that providing locking screws made from a titanium alloy that have the requisite hardness can reduce or eliminate problems arising from material mismatch between the plate and screw in a bone fixation system.

Accordingly, the present teachings provide for systems, devices, and methods for improved bone fixation. The system can comprise a bone plate and a plurality of variable angle screws. The bone plate can comprise titanium. The bone plate can have a threaded screw hole and a non-threaded screw hole. The threaded screw hole can comprise N internal threads extending along a length of the screw hole that defines a threaded screw hole axis. Each of the plurality of variable angle screws can comprise a threaded head having M threads extending along at least a portion of a length of threaded head and a shaft extending from a distal end of the threaded head. Each of the plurality of variable angle screws can comprise a titanium-molybdenum alloy (TiMo) treated to have a hardness of at least 35 HRC. The M threads of the threaded head of a first screw of the plurality of variable angle screws can cut into the N internal threads of the threaded screw hole at a selected angle relative to the threaded screw hole axis to secure the first screw to the bone plate in locking engagement. A second screw of the plurality of variable angle screws can threadedly engage the bone through the non-threaded screw hole to secure the bone and plate in compressive engagement. In one aspect, M does not equal N.

The present teachings also provide for a bone fastener comprising a head and a shaft extending from the distal end of the head. The head can comprise two threads extending along at least a portion of a length of the threaded head. The two threads have thread starts that can be spaced 180° about a proximal end of the head. At least a portion of at least one of a major diameter and a minor diameter of the threaded head is tapered from a proximal end to a distal end thereof. Each of the two threads can have a thread angle of at least 90°. The bone fastener can be formed from a TiMo alloy treated to have a hardness of at least 35 HRC. The distal portion of the shaft can also comprise a drill portion. The drill portion can include a blade comprising a cutting lip and a relief surface trailing from the cutting lip and having a trailing edge.

The present teachings also provide for a method of manufacturing an implant comprising: machining the TiMo alloy having a first hardness value and a first % elongation to form the implant; solution annealing, quenching, and ageing the implant to have a second hardness value that can be greater than the first hardness value and a second % elongation that can be both less than the first % elongation and greater than about 3% elongation. In one aspect, the TiMo alloy can be Ti-15Mo. In another aspect, the implant can be a bone fastener.

The present teachings also provide for a method of engaging a bone fastener in bone comprising: drilling a pilot hole through the near cortex of a bone, penetrating the near cortex with a bone fastener via the pilot hole, wherein the bone fastener can be formed from a TiMo alloy treated to have a hardness of at least 35 HRC, and wherein the bone fastener can comprise: a head that can comprise two threads having thread starts that can be spaced 180° apart about a proximal end of the head, wherein at least a portion of at least one of a major diameter and a minor diameter of the threaded head can be tapered from a proximal end to a distal end thereof, wherein the thread angle of each of the two threads can be at least 90°; and a shaft extending from a distal end of the head, wherein the shaft can comprise a helical thread extending from a point proximate a distal end towards a proximal end of the shaft, wherein at least one of a major diameter and a minor diameter of at least a distal portion of the shaft can be tapered to a point on the distal end of the shaft; wherein the distal portion of the shaft can further comprise a drill portion, wherein the drill portion can include a blade comprising a cutting lip and a relief surface trailing from the cutting lip and having a trailing edge; drilling the bone fastener through at least a portion of the far cortex of the bone, wherein the portion of the shaft threadedly engaged with the near cortex and the distal portion of the shaft can cooperate to tap and drive the shaft into the far cortex.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
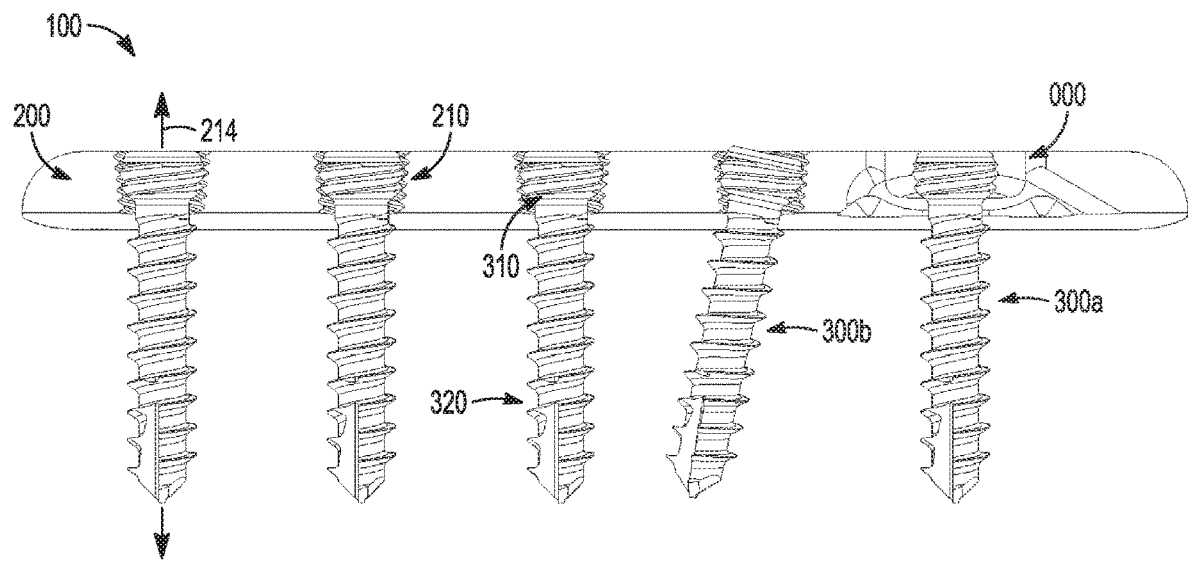
FIG. 1 illustrates a system according to the present teachings.
Figure 2:
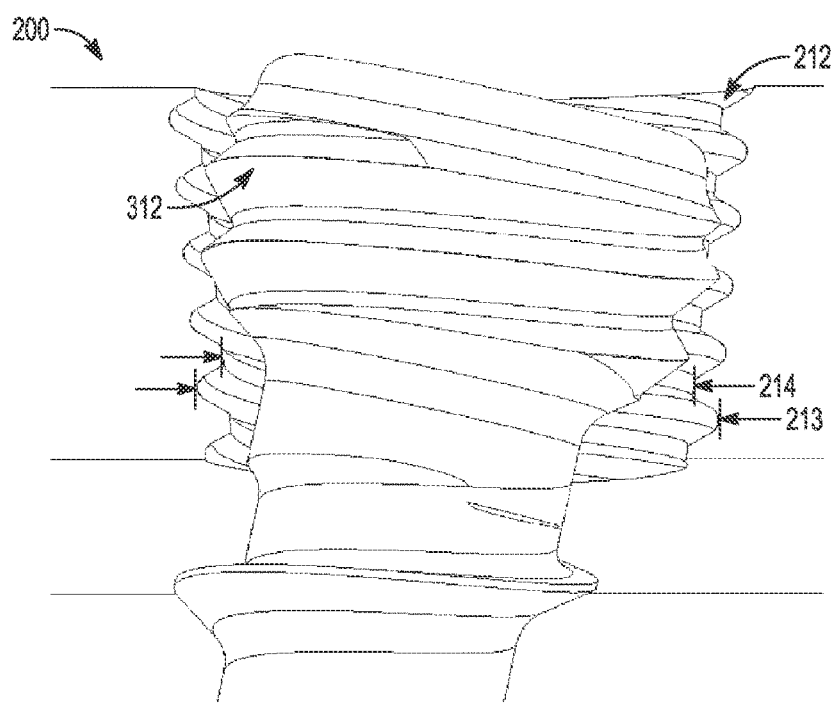
FIG. 2 is a detailed view of a variable angle screw engaged in a threaded hole of an implant.
Figure 3:
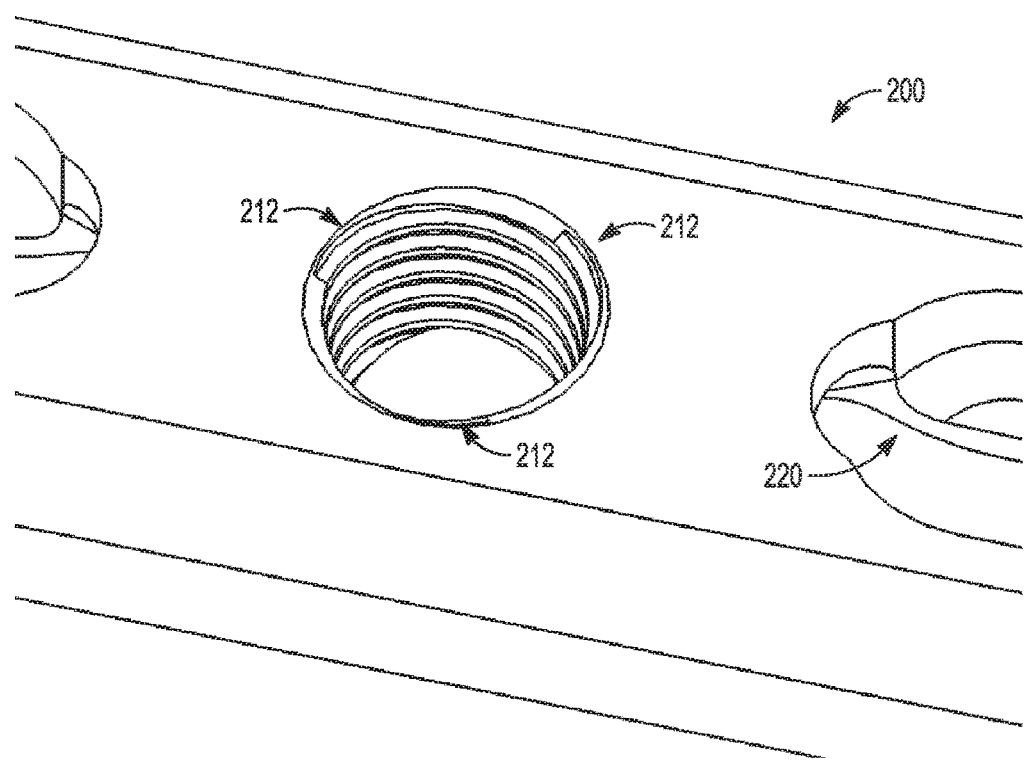
FIG. 3 is a partial perspective view of an implant having a threaded hole and a non-threaded hole.
Figure 4:
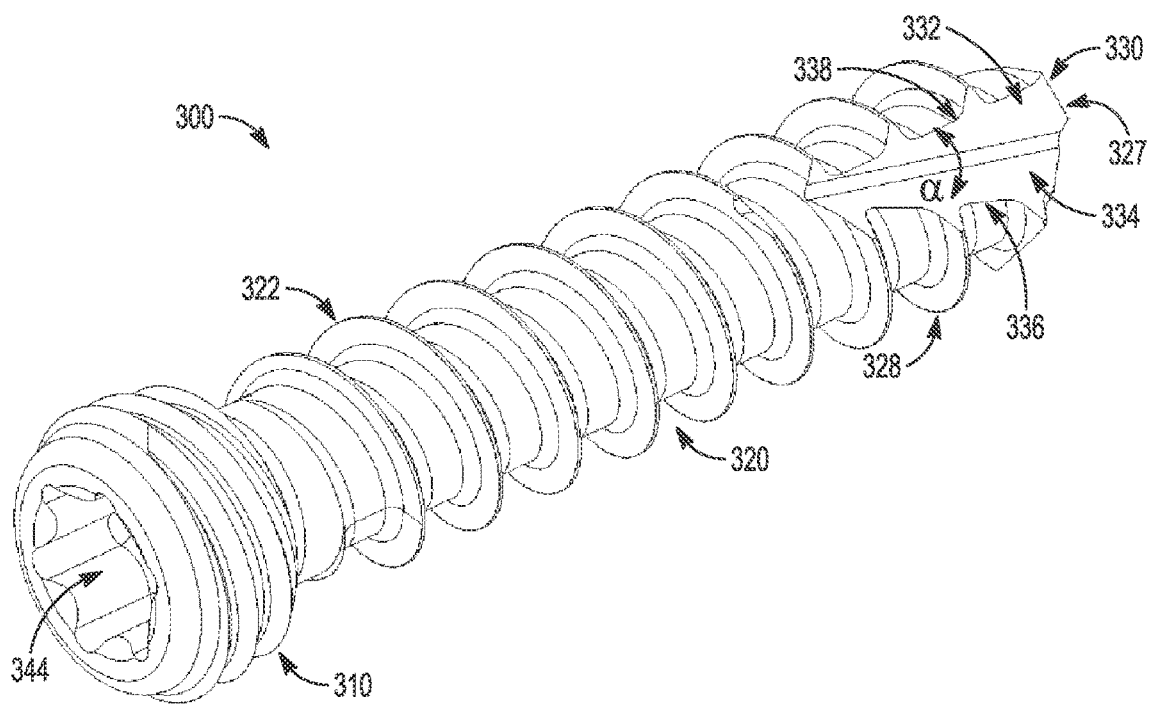
FIG. 4 is a first perspective view of a variable angle screw.
Figure 5:
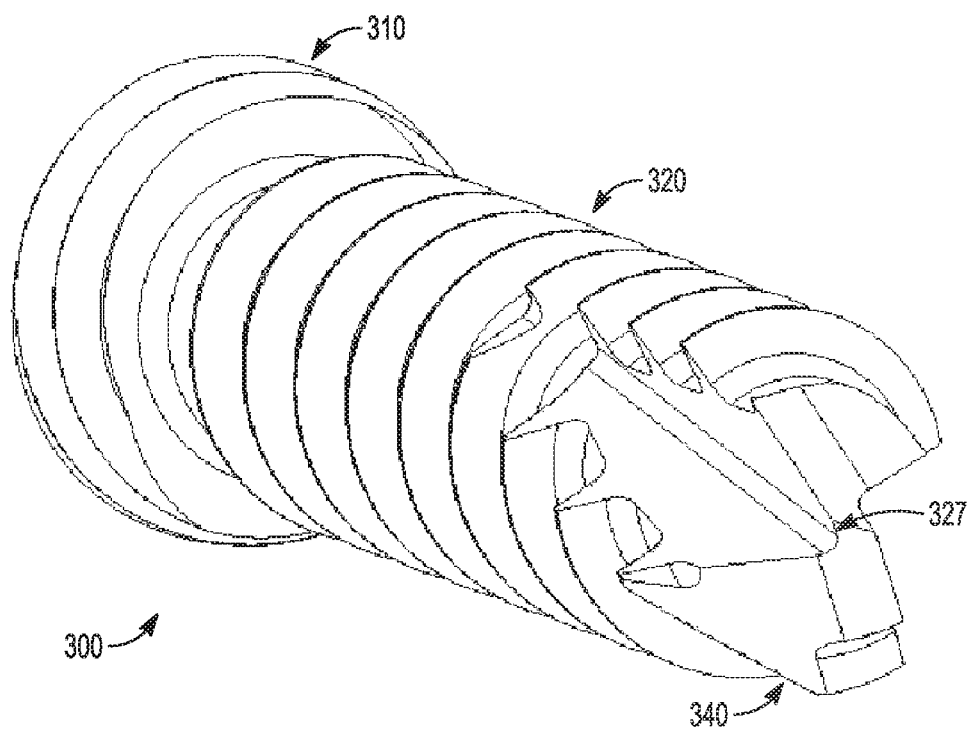
FIG. 5 is a second perspective view of a variable angle screw.
Figure 6:
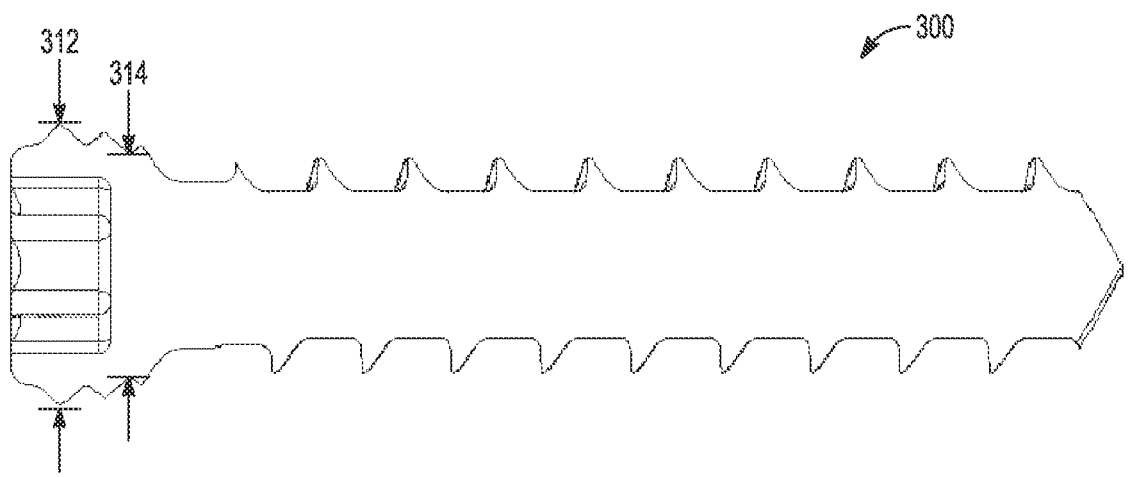
FIG. 6 is a longitudinal cross-sectional view of a variable angle screw.
Figure 7:
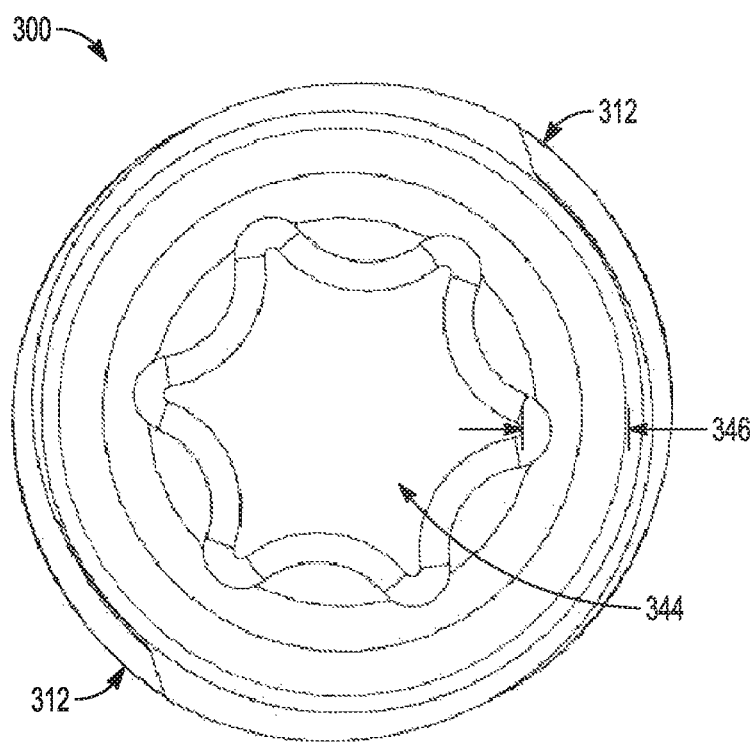
FIG. 7 is a top view of the variable angle screw.

Example embodiments will now be described more fully with reference to the accompanying drawings.

The present teachings provide for devices, systems, and methods for improved bone fixation.

The systems can comprise implants and fasteners that both comprise titanium and minimize or eliminate problems rising from material mismatch. Additionally or alternatively, the systems can comprise an implant and a single type of fastener that can be used both locking and non-locking engagement with the implant and also installed either parallel to or at an oblique angle to an axis of a selected screw hole in the plate.

With initial reference to FIGS. 1-7, a system 100 can comprise a bone plate 200 and a plurality of variable angle screws 300. The bone plate can comprise titanium. The bone plate can further comprise a titanium alloy. The bone plate 200 can have a threaded screw hole 210 and a non-threaded screw hole 220. The threaded screw hole 210 can comprise N internal threads 212 extending along a length of the screw hole that defines a threaded screw hole axis 214. Each of the plurality of variable angle screws 300 can comprise a threaded head 310 and a shaft 320 extending from a distal end of the threaded head 310. The threaded head 310 can comprise M threads 312 extending along at least a portion of a length of the threaded head 310. In one aspect, N does not equal M. In another aspect, N=3 and M=2. Each of the plurality of variable angle screws 300 can comprise a titanium alloy treated to have a hardness of at least 35 HRC. In one aspect, the titanium alloy can be a titanium-molybdenum (TiMo) alloy. In another aspect, the titanium alloy can be Ti-15Mo.

In another aspect, a second screw 300b of the plurality of variable angle screws can threadedly engage the bone through the non-threaded screw hole 220 to secure the bone and plate 200 in compressive engagement. Accordingly, a plurality of variable angle screws 300 can be used in both locking and non-locking engagement and both parallel to and at an oblique angle to the screw hole axis.

In one aspect, the "thread angle" is a feature of a thread defined by the angle between adjacent flanks (i.e., the thread surface extending between the crest and root) measured at a cross-section of the thread. In one aspect, the N internal threads 212 can have a thread angle that can be less than the thread angle of the M threads 312 of the threaded head 310. In one aspect, the N internal threads 212 can have a thread angle of about 60°. In another aspect, the M threads 312 can have a thread angle of greater than 60°. In yet another aspect, the M threads 312 can have a thread angle of from about 90° to about 110°. In yet another aspect, the M threads 312 can have a thread angle of about 100°.

In one aspect, the M threads 312 of the threaded head 310 can comprise two threads having thread starts that can be spaced 180° about a proximal end of the threaded head 310. In another aspect, at least a portion of at least one of a major diameter 312 and a minor diameter 314 of the threaded head 310 can be tapered from a proximal end to the distal end. In another aspect, the major diameter 312 of the threaded head can circumscribe a sphere. In yet another aspect, at least one of a major diameter 213 and a minor diameter 214 of at least a distal portion of the threaded screw hole 210 can be tapered towards the distal end. In another aspect, at least one of the major diameter 213 and the minor diameter 214 of the threaded screw hole can circumscribe a frustocone.

The M threads of the threaded head 310 of a first screw 300a of the plurality of variable angle screws can cut into the N helical internal threads 212 of the threaded screw hole 210 at a selected angle relative to the threaded screw hole axis 214 to secure the first screw 310a to the bone plate 200 in locking engagement. In yet another aspect, when the screw 300 is engaged in the threaded screw hole 210 of the plate 200, the selected angle can be from about 0° to about 30°.

In another aspect, the selected angle can be from about 0° to about 20°.

In one aspect, the shaft 320 of the variable angle screw 300 can be at least partially threaded. In another aspect, a shaft thread 322 can extend from a point proximate a distal end towards a proximal end of the shaft 320. In one aspect, the shaft thread 322 can have a pitch of from about 0.5 mm to about 1.25 mm. In another aspect, the shaft thread 322 can have a pitch of about 1 mm.

In another aspect, at least one of a major diameter 324 and a minor diameter 326 of at least a distal portion of the shaft can be tapered to a point on the distal end of the shaft. In another aspect, the shaft 320 of the variable angle screw 300 can be self-tapping. In an additional or alternative aspect, the variable angle screw 300 can be self-drilling. In one aspect, the point 327 can have a point angle of from about 60° to about 120°. In another aspect, the point 327 can have a point angle of about 90°. In another aspect, the distal portion of the shaft 320 can further comprise a drill portion 328 including a blade 330 comprising a cutting lip 332 and a relief surface 334 trailing from the cutting lip and having a trailing edge 336. In one aspect, the cutting lip 332 and relief surface 334 can define an acute angle 338. In another aspect, the drill portion 328 can comprise two blades 330. In yet another aspect, the two blades can define a flute 340.

In another aspect, the threaded head 310 can have a proximal end 342 that is transverse to a screw longitudinal axis defined by the shaft 320 and a driver aperture 344 defined in the proximal end. The driver aperture can be, for example and without limitation, a slot, a cruciform, a polygon, and the like. The driver aperture can be dimensioned to leave a selected minimum wall thickness 346 between the aperture and the edge of the threaded head to ensure that the maximum torque can be available for installing/removing the screw and that the threaded head 310 will not fail before the shaft 320. As one illustrative example, a screw having a 2.7 mm cortical thread diameter and a 3.51 mm head diameter can have a selected minimum wall thickness of about 0.24 mm. As another illustrative example, a screw having a 3.5 mm cortical thread diameter and a 4.49 mm head diameter can have a selected minimum wall thickness of about 0.48 mm. In yet another aspect, the system 100 further comprises a driver 400 having a distal end that mates with the driver aperture.

Figure 8:
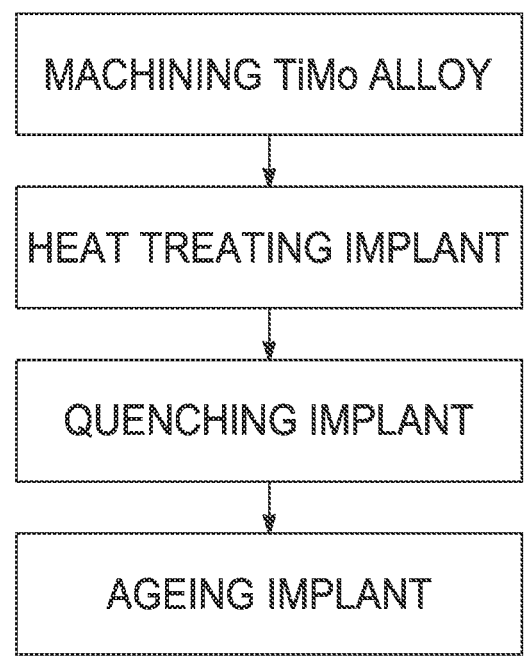
FIG. 8 illustrates a method of manufacturing an implant.

With reference to FIG. 8, the present teachings also provide for a method of manufacturing an implant comprising: machining the TiMo alloy having a first hardness value and a first % elongation to form an implant; heat treating, quenching, and ageing the bone fastener to have a second hardness value that can be greater than the first hardness value and a second % elongation that can be both less than the first % elongation and greater than about 3% elongation. In one aspect, the TiMo alloy can be Ti-15Mo. In another aspect, the implant can be a bone fastener. In another aspect, heat treating the implant can comprise annealing the implant and, in a further aspect, solution annealing the implant. In another aspect, annealing the implant can comprise annealing the implant at a temperature of from about 1300° F. to about 1700° F. In one aspect, the implant can be annealed at about 1650° F. In one aspect, the implant can be annealed at about 1375° F. In another aspect, the implant can be aged from about 3 hours to about 20 hours. In one aspect, the implant can be aged for about 16 hours. In one aspect, the implant can be aged for about 4 hours. In another aspect, the implant can be aged at a temperature of from about 700° F. to about 950° F. In one aspect, the implant can be aged at a temperature of from about 840° F. to about 900° F. In another aspect, the first hardness value can be from about 35 to about 43 HRC. In another aspect, the second hardness value can be from about 43 to about 50 HRC. In one aspect, the second hardness value can be from about 44 to about 46 HRC. In another aspect, the second % elongation can be from about 4 to about 8.

Figure 9:
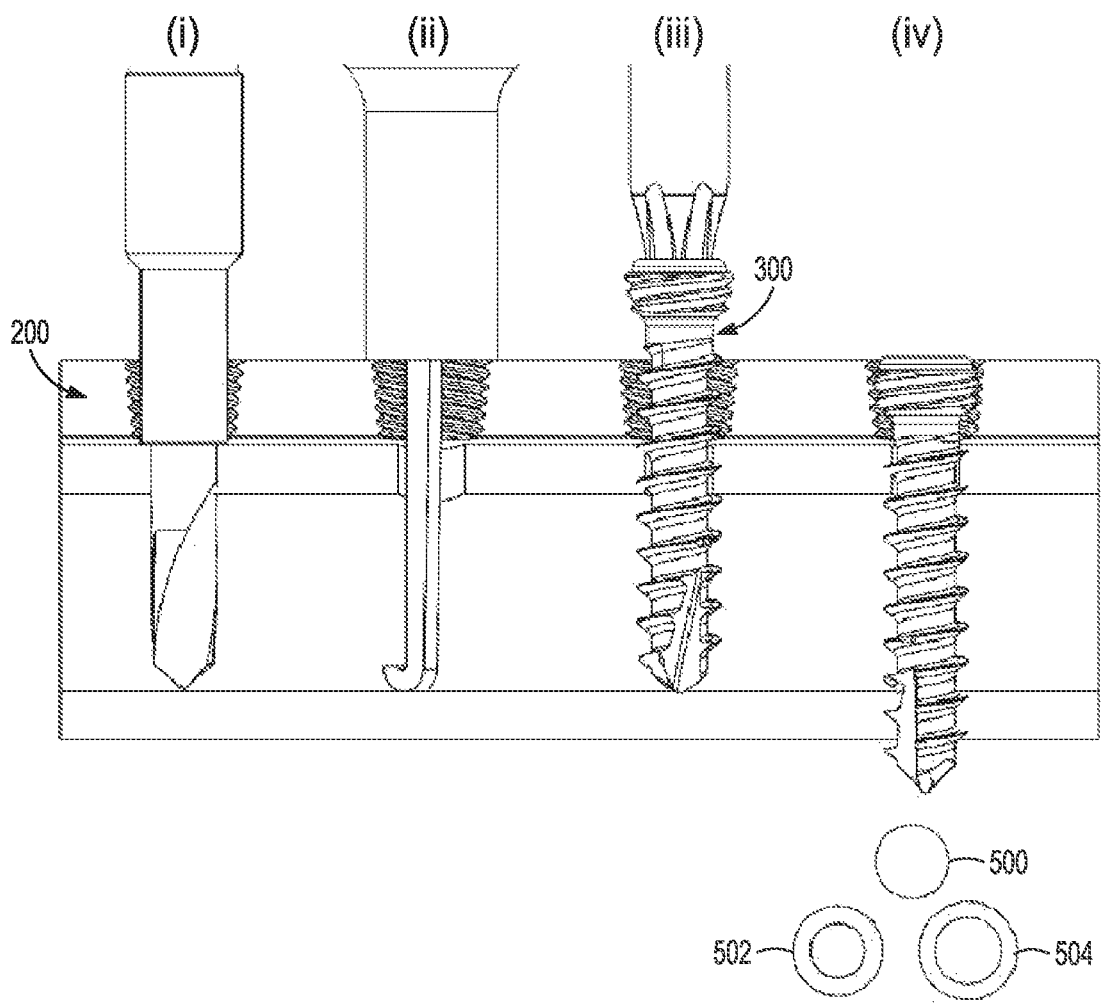
FIG. 9 illustrates a method for engaging a bone fastener.

With reference to FIG. 9, the present teachings also provide for a method of engaging a bone fastener in bone comprising: (i) drilling a pilot hole through the near cortex of a bone, (ii) measuring the distance to the inner surface of the far cortex; (iii) penetrating the near cortex with a bone fastener via the pilot hole, wherein the bone fastener can be formed from a TiMo alloy treated to have a hardness of at least 35 HRC, and wherein the bone fastener can comprise: a head that can comprise two threads having thread starts that can be spaced 180° apart about a proximal end of the head, wherein at least a portion of at least one of a major diameter and a minor diameter of the threaded head can be tapered from a proximal end to a distal end thereof, wherein the thread angle of each of the two threads can be at least 90°; and a shaft extending from a distal end of the head, wherein the shaft can comprise a helical thread extending from a point proximate a distal end towards a proximal end of the shaft, wherein at least one of a major diameter and a minor diameter of at least a distal portion of the shaft can be tapered to a point on the distal end of the shaft; wherein the distal portion of the shaft can further comprise a drill portion, wherein the drill portion can include a blade comprising a cutting lip and a relief surface trailing from the cutting lip and having a trailing edge; (iv) drilling the bone fastener through at least a portion of the far cortex of the bone, wherein the portion of the shaft threadedly engaged with the near cortex and the distal portion of the shaft can cooperate to tap and drive the shaft into the far cortex.

In one aspect, the method for engaging a bone fastener in bone can further comprise a method for securing an implant. In one aspect, the implant can be a plate. In one illustrative example, the method can comprise a method for clavicle fracture fixation. Conventionally, clavicle fracture fixation bears a risk of injury and death due to risk associated with drilling through the far cortex of the clavicle due to the close proximity of important nerves, veins, and arteries. Using the systems, bone fasteners, and methods described herein eliminates the need for drilling through the far cortex and, even if the distal-most end of the bone fastener extends slightly past the far side of the far cortex, the risk of damaging any nerves 500, veins 502 and arteries 504 can be reduced or eliminated.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

Some numbered examples of the present subject matter are listed below:

In Example 1, a bone fixation system can include a bone plate and a plurality of variable angle screws. A bone plate can comprise a threaded screw hole and a non-threaded screw hole. The bone plate can comprise titanium. The threaded screw hole can comprise N internal threads extending along a length of the screw hole that defines a threaded screw hole axis. Each of the variable angle screws can comprise a threaded head and a shaft extending from a distal end of the threaded head. The threaded head can have M threads extending along at least a portion of the length of the threaded. Each of the plurality of variable angle screws can comprise a TiMo alloy treated to have a hardness of at least 35 HRC. In an implanted state, the M threads of the threaded head of a first screw of the plurality of variable angle screws can cut into the N internal threads of the threaded screw hole at a selected angle relative to the threaded screw hole axis to secure the first screw to the bone plate in locking engagement.

In Example 2, the bone fixation system of Example 1 can optionally be configured such that the titanium alloy of the variable angle screw comprises Ti-15Mo.

In Example 3, the bone fixation system of any one or more of Examples 1-2 can optionally be configured such that N does not equal M.

In Example 4, the bone fixation system of Example 3 can optionally be configured such that N=3 and M=2.

In Example 5, the bone fixation system of any one or more of Examples 1-4 can optionally be configured such that the N internal threads of the threaded head comprise two threads having thread starts that can be spaced 180° apart about a proximal end of the threaded head.

In Example 6, the bone fixation system of any one or more of Examples 1-5 can optionally be configured such that at least a portion of at least one of a major diameter and a minor diameter of the threaded head can be tapered from a proximal end to the distal end thereof.

In Example 7, the bone fixation system of Example 6 can optionally be configured such that the major diameter of the threaded head can circumscribe a sphere.

In Example 8, the bone fixation system of any one or more of Examples 1-7 can optionally be configured such that the thread angle of each of the M threads of the threaded head can be greater than 60°.

In Example 9, the bone fixation system of any one or more of Examples 1-8 can optionally be configured such that the thread angle of each of the M threads of the threaded head is from about 90° to about 110°.

In Example 10, the bone fixation system of any one or more of Examples 1-9 can optionally be configured such that the thread angle of each of the M threads of the threaded head can be about 100°.

In Example 11, the bone fixation system of any one or more of Examples 1-10 can optionally be configured such that the thread angle of each of the N threads of the threaded screw hole is about 60°.

In Example 12, the bone fixation system of any one or more of Examples 1-11 can optionally be configured such that at least one of a major diameter and a minor diameter of a distal portion of the threaded screw hole can be tapered towards a distal end thereof.

In Example 13, the bone fixation system of Example 12 can optionally be configured such that at least one of the major diameter and the minor diameter of the threaded screw hole can circumscribe a frustocone.

In Example 14, the bone fixation system of any one or more of Examples 1-13 can optionally be configured such that the shaft can be at least partially threaded.

In Example 15, the bone fixation system of Example 14 can optionally be configured such that a second screw of the plurality of variable angle screws can threadedly engage the bone through the non-threaded screw hole to secure the bone and plate in compressive engagement.

In Example 16, the bone fixation system of any one or more of Examples 14-15 can optionally be configured such that the shaft of each of the plurality of variable angle screws can be self-tapping.

In Example 17, the bone fixation system of any one or more of Examples 14-16 can optionally be configured such that the shaft of each of the plurality of variable angle screws can be self-drilling.

In Example 18, the bone fixation system of any one or more of Examples 14-17 can optionally be configured such that at least one of a major diameter and a minor diameter of at least a distal portion of the shaft can be tapered to a point on the distal end of the shaft and such that a helical thread can extend from a point proximate the distal end towards a proximal end of the shaft.

In Example 19, the bone fixation system of Example 18 can optionally be configured such that the point can have a point angle of from about 60° to about 120°.

In Example 20, the bone fixation system of any one or more of Examples 18-19 can optionally be configured such that the distal portion of the shaft can further comprise a drill portion, wherein the drill portion can include a blade that can comprise a cutting lip and a relief surface trailing from the cutting lip and having a trailing edge.

In Example 21, the bone fixation system of Example 20 can optionally be configured such that the drill portion can comprise two blades.

In Example 22, the bone fixation system of Example 21 can optionally be configured such that the two blades can define a flute.

In Example 23, the bone fixation system of any one or more of Examples 18-22 can optionally be configured such that the cutting lip and relief surface can define an acute angle.

In Example 24, the bone fixation system of any one or more of Examples 14-23 can optionally be configured such that the helical thread can have a pitch of from about 0.5 mm to about 1.25 mm.

In Example 25, the bone fixation system of any one or more of Examples 1-24 can optionally be configured such that the selected angle is from about 0° to about 30° relative to the threaded screw hole axis.

In Example 26, the bone fixation system of any one or more of Examples 1-25 can optionally be configured such that the threaded head can have a proximal end that is transverse to a screw longitudinal axis defined by the shaft and can have a driver aperture defined in the proximal end that can leave a selected minimum wall thickness.

In Example 27, the bone fixation system of any one or more of Examples 15-26 can optionally be configured to include a driver having a distal end that mates with the driver aperture.

In Example 28, the bone fixation system of any one or more of Examples 16-27 can optionally be configured such that the driver aperture can be one of a slot, a cruciform, and a polygon.

In Example 29, a bone fastener can include a head and a shaft extending from a distal end of the head. The head can comprise two threads extending along a length of the head. The two threads can have thread starts that are spaced 180° apart about a proximal end of the head. At least a portion of at least one of a major diameter and a minor diameter of the threaded head can be tapered from a proximal end to the distal end thereof. The thread angle of each of the two threads can be at least 90°. The bone fastener can be formed from a TiMo alloy treated to have a hardness of at least 35 HRC.

In Example 30, the bone fastener of Example 29 can optionally be configured such that the major diameter of the threaded head can circumscribe a sphere.

In Example 31, the bone fastener of any one or more of Examples 29-30 can optionally be configured such that the shaft can comprise a shaft thread that extends from a point proximate a distal end towards a proximal end of the shaft.

In Example 32, the bone fastener of Example 31 can optionally be configured such that at least one of a major diameter and a minor diameter of at least a distal portion of the shaft can be tapered to a point on the distal end of the shaft.

In Example 33, the bone fastener of Example 32 can optionally be configured such that the point can have a point angle of from about 60 to about 120.

In Example 34, the bone fastener of any one or more of Examples 32-33 can optionally be configured such that the distal portion of the shaft can further comprise a drill portion, wherein the drill portion can include a blade comprising a cutting lip and a relief surface trailing from the cutting lip and having a trailing edge.

In Example 35, the bone fastener of Example 34 can optionally be configured such that the drill portion can comprise two blades.

In Example 36, the bone fastener of any one or more of Examples 34-35 can optionally be configured such that the two blades can define a flute.

In Example 37, the bone fastener of any one or more of Examples 34-36 can optionally be configured such that the cutting lip and relief surface can define an acute angle.

In Example 38, the bone fastener of any one or more of Examples 31-37 can optionally be configured such that the shaft thread can have a pitch of from about 0.5 mm to about 1.25 mm.

In Example 39, the bone fastener of any one or more of Examples 29-38 can optionally be configured such that the threaded head can have a proximal end that is transverse to a screw longitudinal axis defined by the shaft and can have a driver aperture defined in the proximal end that can leave a selected minimum wall thickness.

In Example 40, the bone fastener of any one or more of Examples 29-39 can optionally be configured such that the TiMo alloy of the variable angle screw can comprise Ti-15Mo.

In Example 41, a method for engaging a bone fastener can include: drilling a pilot hole through the near cortex of a bone, penetrating the near cortex with a bone fastener via the pilot hole, wherein the bone fastener can be formed from a TiMo alloy treated to have a hardness of at least 35 HRC, and wherein the bone fastener can comprise: a head that can comprise two threads having thread starts that are spaced 180° apart about a proximal end of the head, wherein at least a portion of at least one of a major diameter and a minor diameter of the threaded head can be tapered from a proximal end to the distal end thereof, wherein the thread angle of each of the two threads can be at least 90°; and a shaft that can extend from a distal end of the head, wherein the shaft can comprise a helical thread that can extend from a point proximate a distal end towards a proximal end of the shaft, wherein at least one of a major diameter and a minor diameter of at least a distal portion of the shaft can be tapered to a point on the distal end of the shaft; wherein the distal portion of the shaft can further comprise a drill portion, wherein the drill portion can include a blade that can comprise a cutting lip and a relief surface trailing from the cutting lip and having a trailing edge; drilling the bone fastener through at least a portion of the far cortex of the bone, wherein the portion of the shaft threadedly engaged with the near cortex and the distal portion of the shaft can cooperate to drive the shaft into the far cortex.

In Example 42, the subject matter of Example 41 can optionally be configured such that the TiMo alloy can be Ti-15Mo.

In Example 43, a method for manufacturing an implant can include: machining a TiMo alloy having a first hardness value and a first % elongation to form an implant; solution annealing, quenching, and ageing the implant to have a second hardness value that is greater than the first hardness value and a second % elongation that is both less than the first % elongation and greater than about 3% elongation.

In Example 44, the subject matter of Example 43 can optionally be configured such that the TiMo alloy can be Ti-15Mo.

In Example 45, the subject matter of any one or more of Examples 43-44 can optionally be configured such that annealing the implant can further comprise solution annealing the implant at a temperature of from about 1300° F. to about 1700° F.

In Example 46, the subject matter of Example 45 can optionally be configured such that the implant can be annealed at about 1650° F.

In Example 47, the subject matter of any one or more of Examples 45-46 can optionally be configured such that the implant can be annealed at about 1375° F.

In Example 48, the subject matter of any one or more of Examples 43-47 can optionally be configured such that the implant can be aged from about 3 hours to about 20 hours.

In Example 49, the subject matter of Example 48 can optionally be configured such that the implant can be aged for about 16 hours.

In Example 50, the subject matter of any one or more of Examples 48-49 can optionally be configured such that the implant can be aged for about 4 hours.

In Example 51, the subject matter of any one or more of Examples 43-50 can optionally be configured such that the implant can be aged at a temperature of from about 700° F. to about 950° F.

In Example 52, the subject matter of Example 51 can optionally be configured such that the implant can be aged at a temperature of from about 840° F. to about 900° F.

In Example 53, the subject matter of any one or more of Examples 43-52 can optionally be configured such that the first hardness value can be from about 35 to about 43 HRC.

In Example 54, the subject matter of any one or more of Examples 43-53 can optionally be configured such that the second hardness value can be from about 43 to about 50 HRC.

In Example 55, the subject matter of Example 54 can optionally be configured such that the second hardness value can be from about 44 to about 46 HRC.

In Example 56, the subject matter of any one or more of Examples 43-55 can optionally be configured such that the second % elongation can be from about 4 to about 8.

In Example 57, the subject matter of any one or more of Examples 43-56 can optionally be configured such that the implant can be a bone fastener.

Each of these non-limiting examples can stand on its own, or can be combined in various permutations or combinations with one or more of the other examples.

What is claimed is:

1. A bone fixation system, comprising:
   a bone plate defining a threaded screw hole that extends through the bone plate along a threaded screw hole axis; and
   a variable angle screw configured to attach to the bone plate by engaging the threaded screw hole of the bone plate, the variable angle screw comprising a threaded head having M threads that extend along at least a portion of a length of the threaded head, the variable angle screw comprising a shaft that extends from a distal end of the threaded head, the variable angle screw being formed from a TiMo alloy treated to have a hardness of at least 35 HRC, the variable angle screw being configured to lockingly engage the threaded screw hole in the bone plate such that when lockingly engaged, the M threads of the threaded head cut into N internal threads of the threaded screw hole at a selected angle relative to the threaded screw hole axis.

2. The bone fixation system of claim 1, wherein the selected angle is between 0 degrees and 30 degrees relative to the threaded screw hole axis.

3. The bone fixation system of claim 1, wherein N does not equal M.

4. The bone fixation system of claim 1, wherein N equals three and M equals two.

5. The bone fixation system of claim 1, wherein the N internal threads of the threaded head comprise two threads having thread starts that are spaced 180 degrees apart about a proximal end of the threaded head.

6. The bone fixation system of claim 1, wherein at least a portion of at least one of a major diameter or a minor diameter of the threaded head is tapered from a proximal end of the threaded head to the distal end of the threaded head.

7. The bone fixation system of claim 6, wherein the major diameter of the threaded head circumscribes a sphere.

8. The bone fixation system of claim 1, wherein each of the M threads of the threaded head has a thread angle between 90 degrees and 110 degrees.

9. The bone fixation system of claim 1, wherein each of the M threads of the threaded head has a thread angle of 100 degrees.

10. The bone fixation system of claim 1, wherein each of the N threads of the threaded screw hole has a thread angle of 60 degrees.

11. The bone fixation system of claim 1, wherein at least one of a major diameter or a minor diameter of a distal portion of the threaded screw hole is tapered towards a distal end of the threaded screw hole.

12. The bone fixation system of claim 11, wherein at least one of the major diameter or the minor diameter of the threaded screw hole circumscribes a frustocone.

13. The bone fixation system of claim 1, wherein the shaft of the variable angle screw is at least one of self-tapping, self-drilling, or at least partially threaded.

14. The bone fixation system of claim 13, wherein:
at least one of a major diameter or a minor diameter of at least a distal portion of the shaft is tapered to a first point on the distal end of the shaft, the first point shaped to have a point angle between 60 degrees and 120 degrees; and
the shaft further includes a helical thread extending from a second point proximate the distal end of the shaft toward a proximal end of the shaft, the helical thread having a pitch between 0.5 mm and 1.25 mm.

15. The bone fixation system of claim 14, wherein the distal portion of the shaft further comprises a drill portion, the drill portion including a blade that includes a cutting lip and a relief surface trailing from the cutting lip, the cutting lip and relief surface defining an acute angle between the cutting lip and relief surface.

16. The bone fixation system of claim 15, wherein the drill portion includes two blades that define a flute.

17. The bone fixation system of claim 1, wherein the TiMo alloy is Ti-15Mo.

18. The bone fixation system of claim 1, wherein the bone plate is formed from titanium.

19. A method for engaging a bone fastener, the method comprising:
drilling a pilot hole through a near cortex of a bone;
penetrating the near cortex with a bone fastener via the pilot hole, the bone fastener being formed from a TiMo alloy treated to have a hardness of at least 35 HRC, the bone fastener including a head, the head including two threads having thread starts that are spaced 180 degrees apart about a proximal end of the head, at least a portion of at least one of a major diameter or a minor diameter of the threaded head tapering from the proximal end to a distal end thereof, the thread angle of each of the two threads being at least 90 degrees, the bone fastener further including a shaft that extends from the distal end of the head, the shaft including a helical thread that extends from a point proximate a distal end of the shaft towards a proximal end of the shaft, at least one of a major diameter or a minor diameter of at least a distal portion of the shaft tapering to a point on the distal end of the shaft, the distal portion of the shaft further including a drill portion, the drill portion including a blade, the blade including a cutting lip and a relief surface trailing from the cutting lip; and
drilling the bone fastener through at least a portion of the far cortex of the bone, such that a portion of the shaft threadedly engaged with the near cortex and the distal portion of the shaft cooperate to drive the shaft into the far cortex.

20. A bone fixation system, comprising:
a bone fastener formed from a TiMo alloy and treated to have a hardness of at least 35 HRC,
the bone fastener including a head,
the head including two threads having thread starts that are spaced 180 degrees apart about a proximal end of the head,
at least a portion of at least one of a major diameter or a minor diameter of the threaded head tapering from the proximal end to a distal end thereof,
the thread angle of each of the two threads being at least 90 degrees,
the bone fastener further including a shaft that extends from the distal end of the head,
the shaft including a helical thread that extends from a point proximate a distal end of the shaft towards a proximal end of the shaft,
at least one of a major diameter or a minor diameter of at least a distal portion of the shaft tapering to a point on the distal end of the shaft,
the distal portion of the shaft further including a drill portion,
the drill portion including a blade,
the blade including a cutting lip and a relief surface trailing from the cutting lip.

* * * * *